United States Patent [19]

Weisenthal

[11] Patent Number: 4,996,145

[45] Date of Patent: Feb. 26, 1991

[54] METHOD FOR DETECTING IMMUNE-MEDIATED CYTOTOXICITY

[75] Inventor: Larry M. Weisenthal, Huntington Beach, Calif.

[73] Assignee: Oncotech Incorporated, Irvine, Calif.

[21] Appl. No.: 114,085

[22] Filed: Oct. 27, 1987

[51] Int. Cl.$^5$ .................. G01N 33/53; G01N 33/577; C12Q 1/28; C12Q 1/18

[52] U.S. Cl. .................................. 435/7.23; 424/85.1; 424/85.2; 424/85.8; 435/19; 435/28; 435/32; 435/184; 436/63; 436/501; 436/548

[58] Field of Search .................... 435/22.2, 4, 7, 19, 435/28, 32, 184; 436/8, 63, 501, 548, 64; 424/85.1, 85.2, 85.8

[56] References Cited

U.S. PATENT DOCUMENTS 4,758,549 7/1988 Mitsuhashi et al. .............. 435/172.2
4,778,879 10/1988 Mertelsman et al. ................ 530/351

OTHER PUBLICATIONS

Weisenthal et al., Recent Results in Cancer Research, vol. 94, pp. 161-173, 1984.
Weisenthal et al., Cancer Research, vol. 43, pp. 258-264, Jan. 1983.
Weisenthal et al., Cancer Research, vol. 43, pp. 749-754, Feb. 1983.
Kimber et al., Expl. Cell. Biol., vol. 53, pp. 69-84, 1985.
Rabinowich et al., Cancer Research, vol. 47, pp. 173-177, Jan. 1987.
Endo et al., Cancer Research, vol. 47, pp. 1076-1080, Feb. 1987.
Durkin et al., Cancer Research, vol. 39, pp. 402-407, 1979.
Weisenthal et al., Cancer, vol. 51(8), Apr. 15, 1983, pp. 1490-1495.
Fahey et al., Annals of Internal Medicine, vol. 106, 1987, pp. 257-274.
Weisenthal, Seminars in Oncology, vol. 8(4), Dec. 1981 pp. 362-376.
Weisenthal et al., Clinical Investigations, AACR Abstracts, No. 614, p. 155, vol. 22(8), 1981.
Weisenthal et al., Proceedings of AACR, vol. 27, Mar. 1986, p. 393, No. 1560.
Dolan et al., Proceedings of AACR, vol. 27, Mar. 1986, p. 100, No. 394.
Gambacorit-Passerini et al., Cancer Research 47; 2547-2552 (1987), "Lysis by Activated Lymphocytes of Melanoma and Snall Cell Lung Cancer Cells Surviving in Vitro Treatment with Mafosfamide".
Weisenthal et al., Cancer Treat. Rep. 70:1283-1295 (1986), "Laboratory Detection of Primary and Acquired Drug Resistance in Human Lymphatic Neoplasms".
Weisenthal et al., Cancer Treat. Rep. 71(12): 1239-1243 (1987), "Perturbation of In Vitro Drug Resistance in Human Lymphatic Neoplasms by Combinations of Putative Inhibitors of Protein Kinase C".
Bosanquet et al., "An Assessment of a Short-Term Tumour Chemosensitivity Assay in Chronic Lymphcytic Leukaemia," Br. J. Cancer 47:781-789.
Bosanquet et al., "Short-Term Tumour Chemosensitivity Assay for Haematological Malignancies: Improved Leukocyte Identification and Comparison of Drug Sensitivities in Blood, Marrow and Lymph Node," in 13th Internatonal Congress of Chemotherapy, Spitzy et al., Eds. Verlag H. Egermann, Vienna, Part 224, pp. 130-133 (1983).
Weisenthal et al. "Clonogenic and Nonclonogenic in Vitro Chemosensitivity Assays," Cancer Treatment Rep. 69(6) 615-632 (1985).

(List continued on next page.)

Primary Examiner—Esther L. Kepplinger
Assistant Examiner—Florina B. Hoffer
Attorney, Agent, or Firm—Sheldon & Mak

[57] ABSTRACT

A method for detecting the sensitivity of tumor cells to immune effector substances by using an assay that distinguishes living tumor cells from dead cells in mixed populations of cells. Acquired resistance to immune effectors used in therapy may be determined and used to identify methods to circumvent such resistance using the method.

20 Claims, 2 Drawing Sheets

OTHER PUBLICATIONS

Bird et al., "In Vitro Determination of Tumour Chemosensitivity in Haematological Malignancies," *Hematological Oncology* 3:1–9 (1985).

Bird et al., "The Influence of Sample Source and Cell Concentration on the In Vitro Chemosensitivity of Haematological Tumours," *Br. J. Cancer* 55:539–545 (1986).

Bird et al., "Semi-Micro Adaptation of a 4-Day Differential Staining Cytotoxicity (DiSC) Assay for Determining the In-Vitro Chemosensitivity of Haematological Malignancies," *Leukemia Res.* 10(4): 445–449 (1986).

Carmichael et al., "Evaluation of a Tetrazolium—Based Semiautomated Colorimetric Assay: Assessment of Chemosensitivity Testing," *Cancer Research* 47:936–942 (1987).

Carmichael et al., "Evaluation of a Tetrazolium-Based Semiautomated Colormetric Assay: Assessment of Radiosensitivity" *Cancer Research* 47:943–946 (1987).

de Vries et al., "In Vitro Chemosensitivity of Human Lung Cancer for Vindesine," *Eur. J. Cancer Oncol.* 23:55–60 (1987).

Bird et al., "Comparison of In Vitro Drug Sensitivity by the Differential Staining Cytotoxicity (DiSC) and Colony-Forming Assays," *Br. J. Cancer* 55:429–431 (1987).

Su et al., "Selective Enhancement by Menadiol of In Vitro Drug Activity in Human Lymphatic Neoplasms," *Cancer Treatment Rep.* 71(6) 619–625 (1987).

Ruckdeschel et al., "In Vitro Chemosensitivity of Human Lung Cancer Cell Lines," *Cancer Treatment Rep.* 71 (7–8): 697–704 (1987).

Weisenthal et al., "Perturbation of In Vitro Drug Resistance in Human Lymphatic Neoplasms by Combinations of Putative Inhibitors of Protein Kinase C, " *Cancer Treatment Rep.* 71(12): 1239–1243 (1987).

Bosanquet et al., "Determination of Acquired Drug Resistance and Cross-Resistance in Haematological Malignancies" *Biochem. Soc. Transactions 14:620–621 (1986).*

Einhorn et al., "Interferon Exerts a Cytotoxic Effect on Primary Human Mylenoma Cells," *Eur. J. Cancer Clin. Oncol.* 24:1505–1510 (1988).

Weisenthal et al., "A Novel Dye Exclusion Assay for Predicting Response to Cancer Chemotherapy," *Proc. Amer. Assoc. Cancer REs.* 22:155.

Weisenthal et al., "Comparison of 3 In-Vitro Chemosensitivity Assays: Dye Exclusion (DE), Autoradiography (AR), and Agar Cloning (AC), " *Proc. Amer. Assoc. Cancer Res.* 23:184 (Abstr. 723) (1982).

Bosanquet et al., "A Four-Day Method in Vitro for the Prediction of Response to Cytotoxic Drugs in Chronic Lymphocytic Leukaemia and Other Tumors" *Biochem Soc. Trans.* 10:505–506 (abstr.) (1982).

Bosanquet et al., "In Vitro Chemosensitivity in Haematological Tumors (HT)", *Proc. Amer. Assoc. Cancer Res.* 26:362 (Abstr. 1428) (1985).

Ruckdeschel et al., "The Use of Human Lung Cancer Cell Lines for In Vitro Chemosensitivity Testing", *Proc. Amer. Assoc. Cancer Res.* 26:367 (Abstr. 1449) (1985).

Ihde et al., "Feasibility of In Vitro Growth and Chemosensitivity Testing (CT) of Small Cell Lung Cancer (SCLC) Cells in a Prospective Clinical Trial," *Proc. Amer. Assoc. Cancer Res.* 26:369 (Abstr. 1456) (1985).

Weisenthal et al., "Clinical Correlations (CC) of Chemosensitivity (CS) with a Predictive Dye Exclusion Assay (DEA) in Human Lymphatic Neoplasms (LN)," *Proc. Amer. Assoc. Cancer REs.* 26:369 (Abstr. 1457) (1985).

Carmichael et al., "Comparison of Clonogenic and Non Clonogenic Assays in the Assessment of Drug and Radiation Sensitivity," *Proc. Amer. Soc. Clinical Oncol.* 5:176 (Abstr. 65) (1986).

Fine et al., "Increased Phosphorylation of a 20 kD Protein is Associated with Pleiotropic Drug Resistance (PDR) in Human Small-Cell Lung Cancer (SCLC) Line," *Proc. Amer. Soc. Clinical Oncol.* 5:17 (Abstr. 68) (1986).

Gazdar et al., "Drug Sensitivity Testing (DST) Patterns of Small Cell Lung Cancer (SCLC) Cultures: Correlation with Clinical Response," *Proc. Amer. Soc. Clinical On col.* 5:179 (Abstr. 700) (1986).

Wilbur et al., "Chemosensitivity Guided Chemotherapy of Non-Small Cell Lung Carcinoma. Updating a Pilot Study Using a Dye Exclusion Assay," *Proc. Amer. Soc. Clinical Oncol.* 5:179 (Abstr. 703) (1986).

Weisenthal et al., "Laboratory Detection and Circumvention of Drug Resistance (DR) in Hyman Lymphatic Neoplasms (LN)", *Proc. Amer. Assoc. Cancer Res.* 27:393 (Abstr. 1560) (1986).

METHOD FOR DETECTING IMMUNE-MEDIATED CYTOTOXICITY

FIELD OF THE INVENTION

This invention relates to in vitro diagnostic procedures for immune therapy. In particular, it relates to in vitro tests to detect immune-mediated cytotoxicity using immune effector substances and to methods for detecting sensitivity or resistance to such substances in human subjects.

BACKGROUND OF THE INVENTION

Therapeutic treatments of human cancer using immune intervention are assuming a role of increasing importance Fahey et al., *Ann. Intern. Med.* (1987)) 106:257-74. These therapies include the use of lymphokines and lymphokineactivated effector cells, monoclonal antibodies and interferons. Additionally, certain types of immune-effector cells exhibit spontaneous cytotoxicity in the absence of specific lymphokine stimulation. (Rabinowich et al., *Cancer Research* 47:173-177 (1987)).

Immune intervention, at present, elicits a positive response in only about 1 out of 3 subjects even in cancers which are most successfully treated using this approach. It is evident that a tool for predicting the success or failure of a proposed biological response modification protocol would be of value in preventing unneeded suffering in individuals from ineffective treatment and in selecting from among various alternative protocols that which has the highest likelihood of success.

One approach to an in vitro method for prediction of cytotoxicity is based on the observation that immune-mediated cell damage includes disruption of membrane integrity which leads to cell lysis (Kimber and Moore, *Exp. Cell Biol.* 53:69-84 (1985)). Therefore it would appear that immune-mediated cell damage caused by immune-effector treatment could be based upon a determination of membrane integrity. The two most widely used assays having indications of membrane damage as endpoints are various dye exclusion and chromium 51 release assays (Endo et al., *Cancer Research* 47:1076-80 (1987); Gambacorti-Passerini et al., *Cancer Research* 47:2547-2552 (1987)). Dye exclusion assays are based on the ability of viable cells in the presence of a physiological salt solution, to exclude a dye which is taken up by cells killed through membrane lysis, so that cell death may be quantified in vitro. (See, e.g. Durkin et al., *Cancer Res.* 39:402-407 (1978)). Dye exclusion assays are typically performed by counting preparations of cells in the presence of a dye such as trypan blue, eosin, erythrocin-B, Fast-Green or nigrosin. Living cells, but not dead cells, exclude the dye. The chromium 51 release assay uses the radioactive substance chromium 51 to label cells, for example, tumor cells; $Cr^{51}$ release indicates damage to the cell membrane.

Both of the foregoing assays yield reasonable results when the cell populations to which they are applied are homogeneous. However, non-tumor cells (macrophages, lymphocytes, mesothelial cells and other normal elements) frequently outnumber the tumor cells which are present in human neoplasms. In diseases such as multiple myeloma and acute leukemia the neoplastic cells may only represent 10% of the total cell population present. Standard dye exclusion assays, whether based on trypan blue and light microscopy or propidium iodide and flow cytometry suffer from several disadvantages, including poor ability to discriminate between effects on tumor and non-tumor cells. Additional difficulties with standard dye exclusion assays have been described ((Weisenthal et al., *Cancer Res.* 43:258-264 (1983)). The $Cr^{51}$ assay also fails to distinguish between normal and tumor cells.

In addition, there is a great deal of spontaneous chromium 51 release by cells, whether alive or dead, occasionally exceeding 50% over a three hour period. Thus, it is very difficult to determine with precision how much chromium release is due to the drug and how much is caused by damage to tumor cells as opposed to non-tumor cells. Finally, because of the rapid spontaneous release, the duration of the assay is constrained to a period of only several hours. This mandates the use of large concentrations of the immune effectors.

An in vitro assay (the differential staining cytotoxicity or "DiSC" assay) which permits prediction of the chemosensitivity of human tumors to various drugs, without requiring tumor growth in culture, has been reported (Weisenthal et al., *Cancer* 51:1490-1495 (1983); and Weisenthal et al. in *Recent Results in Cancer Research*, 94:161-173, Springer Verlag, Berlin-Heidelberg (1984)). The DiSC assay, further described below as readily adaptable to the method of the present invention, permits discrimination of cytotoxic effects between tumor and non-tumor cell populations co-existing in the same cell suspension. The co-existence may be advantageous, since it more realistically mimics the situation in vivo. This assay relies on the ability of living cells to exclude certain dyes such as Fast Green, Nigrosin or the combination of Fast Green and Nigrosin, while dead cells cannot. Living cells may be counterstained, for example with Wright Giemsa (hematologic neoplasms) or hematoxylin and eosin stain (solid tumors) to facilitate counting. The number of individual cells capable (or not) of dye uptake is ascertained by a technician counting cell populations using a microscope. Thus the assay provides a means for individually counting the number of tumor cells surviving in the presence or absence of a chemotherapeutic agent when the biopsied tumor cells are subjected to the assay. Methods for monitoring human patients for acquisition of resistance to chemotherapeutic drugs and for designing alternative programs of chemotherapy for tumors which become resistant to the drug using the DiSC assay, have been reported (Weisenthal et al., *Cancer Treat Rep.* 70:1283-1295 (1986); and Weisenthal et al., *Cancer Treat Rep.*, In Press, Nov. 1987).

Immune therapies are very expensive, frequently toxic and only sporadically effective. It would thus be beneficial to provide a method for in vitro prediction of the probable clinical efficacy of immune effector substances and the ability to thereafter monitor patients for acquisition of resistance to such therapies, as well as to design modification of treatments to overcome such resistance. The method could be used to determine the most promising strategies of immune interventions in cancer and other disease states. Such a method is provided by the invention herein.

SUMMARY OF THE INVENTION

The invention provides a method for detecting the sensitivity of tumor cells to immune effectors using an in vitro assay and is predictive of response of the corresponding tumor to these effectors in vivo. The method may also be used to monitor individual subjects for acquisition of resistance to immune effectors that may be administered in their particular therapy programs, and to predict the success of alternative programs to which the tumors are still sensitive.

The method is based on the withdrawal of fresh tumor cell samples from the subject and assessing the identified tumor cells microscopically in vitro for sensitivity to the test immune effectors. For monitoring the acquisition of resistance, the tumor cells are tested for short term sensitivity to the immune effectors used in the therapeutic regime of the subject. If resistance is found, the assay can be used to predict the effects of modifying substances which may render the previously administered therapeutic agents effective, or to predict the sensitivity of the patients' cells to alternative therapeutic substances.

DETAILED DESCRIPTION OF THE INVENTION

Figure 1:
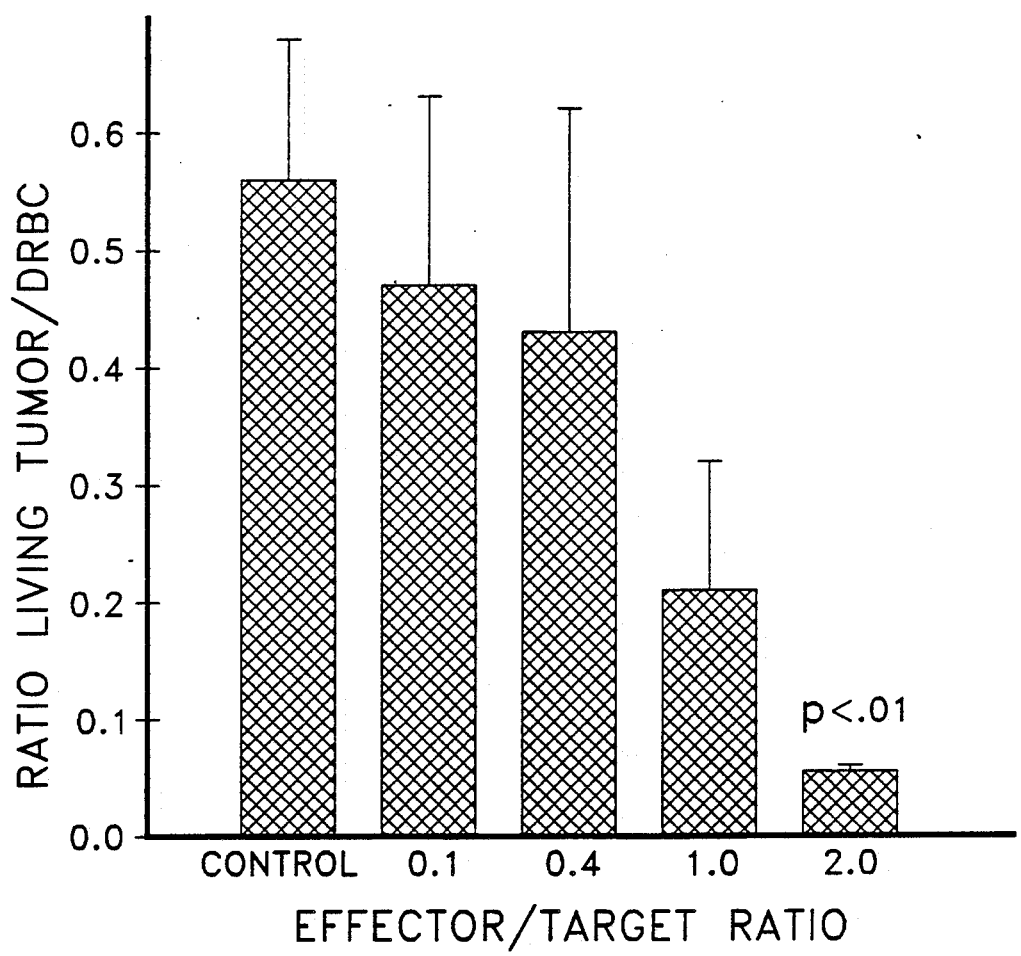
FIG. 1 is a bar graph depicting the sensitivity of undifferentiated small cell carcinoma cells to lymphocytes stimulated by exposure to Il-2 after seven days incubation detected using the method of the invention.

The method of the invention relies on an in vitro assay procedure (the DiSC assay) to test for sensitivity (cell kill) of fresh tumor cells obtained from human patients to individual immune effectors. Additionally, for monitoring resistance of tumor cells to specific immune effector cells are withdrawn from patients being subjected to treatment over time, in order to evaluate the continued effectiveness or lack thereof of a particular effector. For patients where increased resistance to a specific effector protocol is found, fresh tumor samples may be evaluated using the in vitro assay for their sensitivity either to the same effector in combination with some modifying agent, or to new effectors entirely. By such redesign, the treatment of the patient can be modified to accomodate the resistance acquired.

General Methods

The method depends on the use of an in vitro assay which permits the effects of test materials on tumor cells to be distinguished from those on normal cells in the same preparation. The assay should also employ an internal standard so that recovery of the requisite number of cells for measurement can be identified. The DiSC assay as described in Weisenthal et al., *Cancer Treatment Reports, supra*, incorporated by reference herein has these advantages. The assay is performed as follows:

Sample preparation depends on the nature of the sample being taken, and follows standard guidelines for obtaining specimens for human studies. For example, depending on the nature of the tumor, specimens may include EDTA-anticoagulated blood or bone marrow specimens and solid tumor biopsy specimens. Solid tumors are collected in complete tissue culture medium with antibiotics. Cells are manually teased from the tumor specimen or, where necessary, are enzymatically disaggregated by incubation with collagenase/DNAse and suspended in appropriate media containing, for example, human or animal sera.

For the assay, bone marrow specimens, peripheral blood buffy coats (approximately 1 cm$^3$), or other appropriate tumor cell specimens are diluted with 6–10 volumes of complete RPMI-1640 medium containing 10 units/ml of heparin. This is underlayered with Ficoll-diatrizoate (Lymphocyte Separation Medium, Litton Bionetics, Kensington, MD) and centrifuged. The interface layer is washed and counted. Cells (0.1-1×10$^6$, depending on cell yield) are aliquoted into 0.8 to 4 ml capacity conical polypropylene tubes to allow for maintenance of cell-cell interactions that may be involved in the mechanism of immune effector action, and brought to a volume of 0.1 ml with complete RPMI-1640 medium plus 10% heat-inactivated fetal calf serum; 0.01 to 0.1 ml of 10 X effector preparation is added to the test cell suspensions, and cells are incubated for various time periods, for example, 1 hr., 3 hr., 4 days, 7 days or 14 days.

After the predetermined time in culture, 0.01 to 0.2 ml of a suspension of acetaldehyde-fixed duck red blood cells (DRBC), containing from 30,000 to 50,000 DRBC as an internal standard, is added to each tube, and the cells are concentrated if necessary to a final volume of 0.1 to 0.2 ml by centrifugation. Following this, 0.01 to 0.2 ml of Fast Green (solid tumors) or Fast Green-Nigrosin (hematologic neoplasms) (1.0% Fast Green and 0.5% Nigrosin) in 0.15 M NaCl is added and the tubes are vortexed. After 10 minutes, cell suspensions are again vortexed and cytocentrifuged (1200 rpm on a Cytospin I (Shandon Southern Instruments, Inc., Sewickley, PA) or 1080 rpm on a Cytospin II) for 8 minutes. The cell disks are then counterstained with hematoxylin and eosin (H&E) (solid tumors) or are fixed with methanol for 20 seconds and counterstained with Wright-Giemsa (hematologic neoplasms). Mounting balsam (Histomount, National Diagnostics, Somerville, NJ) and coverslips are added. Slides are then counted at either 400 X or 1000 X on a standard light microscope by a trained hematology technologist.

"Living" cells stain with H&E or Wright-Giemsa. "Dead" cells stain green with Fast Green and black or black-green with Fast Green-Nigrosin. DRBC stain green and are easily identified as nucleated microelliptocytes. Only "living" tumor cells and DRBC are counted. The "living" tumor cells/DRBC ratio is determined, and the ratios from cultures subjected to the effector protocol are compared with the ratios from control cultures (cultures containing vehicle, usually 0.9% NaCl) and expressed as percent of control. If desired, a similar procedure can be followed to identify the comparative effects of immune effector substances on normal cell populations present in most fresh tumor preparations.

While the invention is not limited to use of the specific foregoing in vitro assay method, this method has been shown to be highly reliable and useful. A large percentage of assays performed using this method are "successful". A "successful" assay is defined as an assay in which at least 100 viable and recognizable neoplastic cells are present on the control slides and in which a result could be obtained for three or more biologics. In practice, dozens of biologic agents can be tested in a typical assay.

The method of the invention detects disruption of membrane integrity in response to the use of biological agents generally known in the art including lymphokines, effector cells, monoclonal antibodies and interferons. Lymphokines include, for example, IL-2, TNF, CSF-1, G-CSF, GM-CSF, lymphotoxin-3 and human IL-3. Effector cells include macrophages, lymphocytes and other hematopoietic cells. Combinations of these materials may also be used such as lymphocytes in combination with IL-2. The various parameters of the assay for performing the method including the amount of the effector or effector combination and time of incubation of tumor cells with the effectors may be predetermined experimentally for each selected agent.

Because the assay method relies on distinguishing individual cells, the assay may also be used to provide, for example, insight into the mechanism by which the immune effectors achieve cytotoxicity. Stains that are specific for certain types of tumor cells, for example periodic acid Schiff or mucicarmine which stain mucin-containing cells, or myeloperoxidase or chloracetate esterase which stain leukemia cells, may be used to distinguish various tumor cell types in tumor specimens. [$^3$H]-thymidine autocell radiography may be combined with the staining procedure to discriminate between killing of dividing versus non-dividing cells.

Furthermore, stains or other labeling agents used to detect binding of effectors to tumor cells or other significant endpoints may be used in conjunction with the differential staining. For example, the method of the present invention may be used to investigate binding of monoclonal antibody reactive with tumor-associated antigen to tumor cells. The antibody may be conjugated with a toxin such as ricin A or diptheria toxin and immunoperoxidase stain specific for the conjugate or a portion thereof may be used to study the conjugate binding to, and response of, the tumor cells. The appropriate immunoperoxidase is a conjugate of antibody reactive with a relevant ligand such as ricin, and an enzyme (peroxidase) that produces a (brown) color when exposed to its substrate (e.g. orthophenylene-diamine "OPD"). This immunoperoxidase stains the antibody-toxin conjugate brown, which will be distinguishable from the staining of live and dead cells in the DiSC assay. Cells that stain green and are thus "dead" according to the DiSC assay should have the antibody-toxin conjugate bound and thus also stain brown. Living cells (stained red by the counterstain used in the DiSC assay) may be examined to determine whether the antibody-conjugate did not bind, or whether the toxin did not function; if the cells do not stain brown then the antibody did not bind, if the cells stain brown but did not die, then the toxin was ineffective. Additional stains or labels such as enzymes, radionuclides and fluorescent agents, and cytotoxic agents may be used to provide useful information about the action of selected therapeutic agents and combinations of agents.

Also stained tumor cell preparations may be permanently affixed to cytological slides to permit a detailed study, for example, of the association of target tumor cells and immune effectors, or for study and possible correlation of assay results on the different populations of cells present in a single culture. This expands the range of information obtainable from a simple "will" or "will not work" analysis to permit evaluation of factors which influence success or failure.

The assay may be conducted in as little as several minutes to days. Longer exposure of target tumor cells to the immune effectors is preferred, so that lower (physiological) concentrations of the effector substances may be used to permit the identification of specific cytotoxic effects. Previous methods have required high concentrations of effectors for short term exposures to provide effects detectable over background. Concentrations of the immune effectors and exposure times are determined individually by obtaining preliminary experimental data and correlative in vitro and in vivo responses.

The ability of the assay to detect specific effects of cytotoxic agents also provides a basis for detecting the response of tumor cells to a combined therapeutic program of cytotoxic drugs and immune effectors. Chemotherapeutic drugs are generally known in the art and include, for example, mechlorethamine, melphalan, carmustine, cytarabine, dexamethasone, doxorubicin, cisplatin, etoposide, LPAM and vincristine. Drug concentrations and times of exposure in the assay are determined individually; drugs may be tested at a 1-hour exposure or at a continuous exposure. Thus the assay should be calibrated for different drugs with either a 1-hour or a continuous exposure. Continuous exposures are simpler and the assay can be calibrated on the basis of a continuous exposure for most drugs.

The following examples are presented to illustrate the method of the present invention and to assist one of ordinary skill in making and using the same. The examples are not intended in any way to otherwise limit the scope of the disclosure or the protection granted by Letters Patent granted hereon.

EXAMPLE I

Effect of IL-2 Effector Cells on Tumor Cells

A subcutaneous biopsy specimen was obtained from a 25 year old male patient (San Diego, CA) with an undifferentiated small cell carcinoma of the retroperitoneum. The patient had previously failed combination chemotherapy with cyclophosphomide, vincristine, doxorubicin and dacarbazine (DTIC).

The tissue was removed for unrelated indications and was placed in RPMI 1640 transport media. Cells were incubated at 37° C. overnight in a dilute solution of DNAse/collagenase. Cells were then teased from the tumor specimen, suspended in "LAK" media containing RPMI-1640 medium with gentamycin (Irvine Scientific, Irvine, CA) and containing 2% human AB serum. Cells were centrifuged over Ficoll-hypaque, and then resuspended in LAK medium; 40,000 cells in 25 microliters of LAK medium were aliquoted into individual 0.8 ml capacity conical polypropylene microculture tubes.

In the test samples, IL-2 (Amgen, Thousand Oaks, CA) was aliquoted into tubes at concentrations of 74 units per ml and 588 units per ml. Final culture volume was 0.1 ml.

Autologous peripheral blood lymphocytes ("PBL", the effector cells) which had been isolated from the same patient were also added to the culture tubes in amounts of 0, 400, 1600, 4000, and 80,000 cells per tube. Thus effector:target ratios ranged from 0.1 to 2.0. Cells were incubated for 7 days and then were processed according to the DiSC assay method as follows:

After 7 days in culture, 0.01 ml of a 2% Fast Green suspension, containing 50,000 acetaldehyde-fixed duck red blood cells (DRBC), was added to each tube. After 10 minutes, cell suspensions were again vortexed and cytocentrifuged (1200 rpm on a Cytospin I or 1080 rpm on a Cytospin II) for 8 minutes. The cytospin slides were then counterstained with hematoxylin and eosin (H&E). Mounting balsam (Histomount, National Diagnostics, Somervilled, NJ) and coverslips were added. Slides were then counted at 400 X on a standard light microscope by a trained hematology technologist. "Living" cells stained with H&E. "Dead" cells stained green with Fast Green. DRBC stained green, and were easily identified as nucleated elliptocytes.

The cytospin slides demonstrated the presence of small numbers of tumor cells and large numbers of macrophages and variable numbers of untransformed and transformed lymphocytes. The ratios of living tumor cells:DRBC were counted by an experienced technician. Living tumor cells and DRBC were individually enumerated and normal cells, dead cells and transformed lymphocytes were not counted. FIG. 1 is a bar graph of the results. The ratio of living tumor cell:DRBC was determined and plotted on the Y axis opposite the initial effector:target cell ratio on the X axis. Quadruplicate cultures were counted and results are expressed with standard deviations. Significant levels were determined by analysis of variance using the F comparison.

As shown by these results, the method of the invention detected specific tumor cell lysis at very low ratios of effector cells/tumor cells (0.1:1–2.0:1) during a seven day period of co-incubation.

This method is thus applicable for detecting sensitivity to biologics in primary cultures of fresh human tumors which contain heterogeneous mixtures of tumor cells and nontumor cells.

Figure 2:
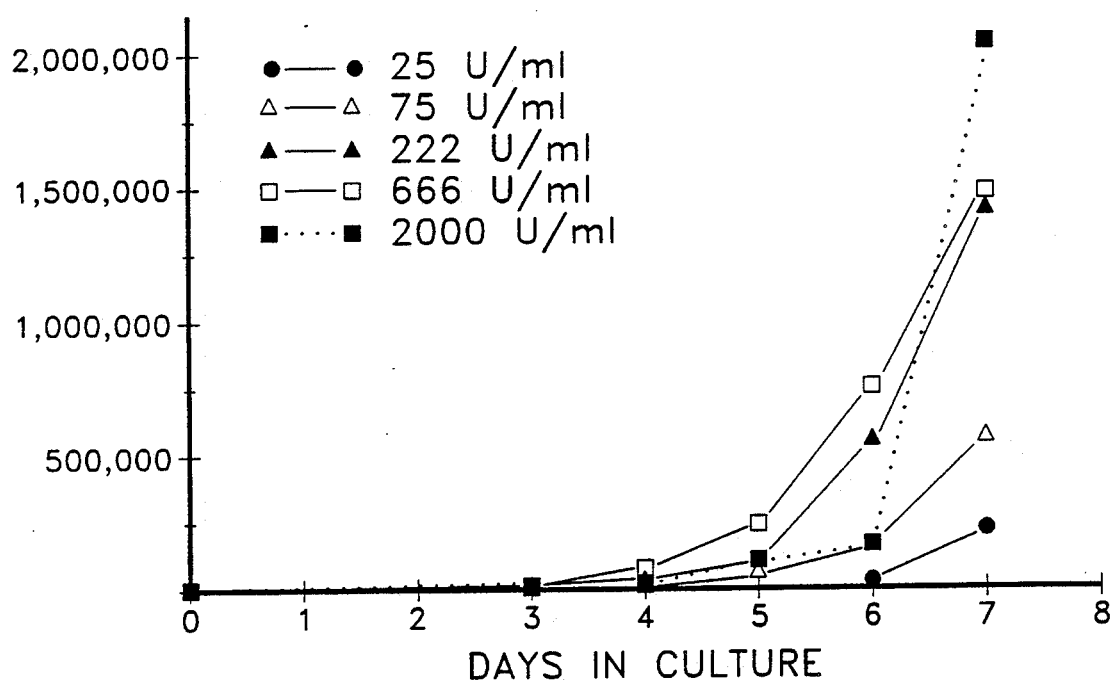
FIG. 2 shows the kinetics of IL-2-mediated lymphocyte transformation.

In addition, since individual cells can be identified, the effect of IL-2 on the effector cells could be verified for various levels of IL-2. In a preliminary assay, PBL effector cells were incubated at varying levels of IL-2 and the number of transformed lymphocytes determined as a function of time (and IL-2 concentration). The large transformed lymphocyte were distinguished from their small untransformed counterparts. The results, as shown in FIG. 2 indicated that at least a 6-day culture period was required for the foregoing assay.

EXAMPLE II

Effective use of in vitro information for detecting the acquired resistance to biological molecule therapy, and in designing effective therapies requires correlation of in vitro results from the protocol selected with in vivo response to the therapy. In vivo data for correlation may be obtained by evaluation of patients by physicians according to standard criteria, for example (50% reduction in the diameter of lymph nodes (e.g. lymphoma), reduction in serum myeloma protein (multiple myeloma) and reversion to chronic myelocytic leukemia (CML) (Blast crisis CML) or complete remission (acute lymphoblastic leukemia (ALL), or 50% reduction in perpendicular diameter of solid tumor masses.

For establishing in vitro correlation with in vivo response, tumor cells are withdrawn at appropriate times and assayed in vitro. The specimens are obtained from both previously untreated and previously treated patients. Single therapeutic agents and combinations of agents, including combinations of immune effector substances and chemotherapeutic drugs such as cisplatin are used to treat patients. The assay results are collected and analyzed to detect onset of resistance of specimens to a particular therapeutic agent.

Prospective clinical correlations are then made from these results for a particular tumor type. For such correlations the following categories are predicted: true positives, i.e. patients whose specimens are sensitive to the therapeutic agent in vitro and to therapy in vivo: false positives, specimens sensitive in vitro, no response to therapy in vivo, true negatives, resistant in vitro, not responsive to therapy in vivo, and false negatives, resistant in vitro, responsive to therapy in vivo.

Results are compared to detect whether in vitro sensitivity to the biological therapies correlates with clinical (in vivo) response.

EXAMPLE III

To detect the acquisition of resistance to the immune effector therapy, or combined immune effector and chemotherapeutic drug therapy, the method of the invention as set forth in Example I is performed on freshly drawn tumor cells withdrawn from patients at intervals who either had not received or had received intervening therapy. These results may be used to compare with in vivo disease states. Metachronous (data taken at two or more different time points) comparisons of the effects of identical concentrations of the therapeutic agent may be made to determine patterns of acquired resistance. Assay results may be classified as "sensitive" or "resistant" (as defined from preliminary experimental data). The assays are performed on patients that have intervening therapy between assays, and those that do not, to attempt to detect resistance patterns. Acquired resistance is indicated by increased resistance in specimens from patients previously treated with a particular therapeutic agent as compared to specimens from previously untreated patients.

EXAMPLE IV

To circumvent acquired resistance, for those patients where increased resistance to the therapeutic regime is detected as set forth in Example III, fresh tumor samples are evaluated using the method of the invention, to detect sensitivity to the same immune effector substance in combination with a modifying agent, or to a new effector or drug entirely. Thus the therapy administered to a resistant patient may be modified to accomodate the resistance acquired. For example, therapy may be changed to an alternative form of therapy (biologic or chemical) or a specific biologic or chemical modulating agent may be identified through the use of the assay (e.g., Weisenthal et al., *Cancer Treat Rep.*, In Press, 1987).

As will be apparent to those skilled in the art in which the invention is addressed, the present invention may be embodied in forms other than those specifically disclosed above, without departing from the spirit or essential characteristics of the invention. Particular embodiments of the present invention described above are therefore to be considered in all respects as illustrative and not restrictive. The scope of the present invention is as set forth in the appended claims rather than being limited to the examples contained in the foregoing description.

What is claimed is:

1. A method for evaluating in vitro the response of tumor cells from a human subject to the presence of an immune effector substance to predict response of the tumor cells in vivo to treatment with the effector substance, which method comprises:
   (a) obtaining a sample from a subject containing fresh tumor cells and non-tumor cells including endogenous effector cells;
   (b) exposing a portion of said sample of tumor and nontumor cells in vitro to an immune effector substance for a time effective to evaluate the response of said tumor cells to the presence of said effector substance by determining whether the tumor cells are killed and leaving a portion of said sample as a control untreated by said effector substance;

(c) adding an internal standard to each of said samples to verify that similar numbers of total cells are present;

(d) adding a dye excluded by living cells to stain cells killed by said immune effector substance;

(e) counterstaining said cells with a stain that indicates living cells to indicate the remaining living tumor cells from non-tumor cells in the sample exposed to said effector substance; and (f) comparing the number of individual tumor cells surviving in the presence of the effector substance, with the numbers of individual tumor cells surviving in the absence of said effector substance, by counting cells able to exclude said dye excluded by living cells, and normalizing to said internal standard distinguishable from said tumor cells, whereby the number of tumor cells killed in response to the presence of said effector substance in vitro is determined and is used to predict the response in vivo of the tumor cells of said subject to said effector substance.

2. The method of claim 1 wherein said internal standard is acetaldehyde-fixed duck red blood cells.

3. The method of claim 1 wherein said step of comparing includes the step of determining the ratio of the number of living tumor cells to the number of internal standard cells in the portion of the sample exposed to said effector substance with the ratio in the portion of the sample not exposed to the immune effector substance.

4. The method of claim 1 wherein said dye is selected form the group consisting of Fast Green and Fast Green-Nigrosin.

5. The method of claim 1 wherein said stain is selected from the group consisting of hematoxylin and eosin, and Wright Giemsa.

6. The method of claim 1 wherein said immune effector substance is selected from the group consisting of lymphokines, lymphokine-activated effector cells, non-lymphokine-activated effector cells, monoclonal antibodies and interferons.

7. The method of claim 1 further comprising adding an indicator substance that indicates the binding of said immune effector substance to said tumor cells.

8. The method of claim 7 wherein said indicator substance is a stain selected from the group consisting of immunoperoxidase, periodic acid Schiff, esterase and mucicarmine.

9. The method of claim 7 wherein said indicator substance is a label selected from the group consisting of enzymes, radionuclides and fluorescent agents.

10. The method of claim 7 wherein said immune effector substance is conjugated with a cytotoxic substance.

11. The method of claim 10 wherein said cytotoxic substance is selected from the group consisting of ricin and diptheria toxin.

12. The method of claim 10 wherein said cytotoxic substance is a radionuclide.

13. The method of claim 1 wherein said cells are also exposed in step (b) to a chemotherapeutic drug.

14. The method of claim 13 wherein said chemotherapeutic drug is selected from the group consisting of mechlorethamine, melphalan, carmustine, cytarabine, dexamethasone, doxorubicin, cisplatin, and vincristine.

15. A method for monitoring changes in resistance to effector substances of tumor cells in patients subjected to therapeutic treatment which method comprises:

(a) periodically withdrawing a sample from a subject containing fresh tumor cells and non-tumor cells including endogenous effector cells;

(b) assaying a portion of said sample in vitro for response to the presence of an immune effector substance by determining the number of individual tumor and normal cells surviving after incubation in the presence of the effector substance as compared to the number of tumor cells surviving in the absence of the effector substance, by identifying and enumerating the cells that exclude a dye excluded by living cells and normalizing to an internal standard, and counterstaining said cells with a stain that indicates living cells; and (c) comparing the response of the later withdrawn tumor cells to that of earlier withdrawn tumor cells to detect diminished response to the immune effector substance indicating that the tumor cells have acquired resistance to said immune effector substances.

16. The method of claim 15 wherein said step of assaying includes the step of determining the ratio of the number of living tumor cells to the number of internal standard cells in the portion of the sample exposed to the effector substance with the ratio in a portion of the sample not exposed to the immune effector substance.

17. A method to successively modify an ongoing therapeutic protocol in a human subject using immune effector substances, which method comprises:

(a) periodically withdrawing a sample containing fresh tumor cells and non-tumor cells including endogenous effector cells from a human subject who has been previously undergoing treatment with an immune effector substance;

(b) assaying in vitro the response of said tumor cells to the presence of an immune effector substance used in the previous therapeutic treatment of the subject by determining the number of individual tumor and normal cells surviving after incubation in the presence of the effector substance as compared to the number of tumor cells surviving in the absence of the effector substance by identifying and enumerating the cells that exclude a dye excluded by living cells and normalizing to an internal standard, and counterstaining said cells with a stain that indicates living cells; and (c) comparing the response of the later-withdrawn tumor cells to that of earlier withdrawn cells; and if diminished response to the effector substance is found, (d) determining the response of said tumor cells to alternative immune effector substance or to the immune effector substance in combination with other therapeutic agents;

(e) modifying the previous therapeutic treatment by administering to the human subject said alternative immune effector substance and/or other therapeutic agents which are shown to cause a response in said tumor cells in step (d).

18. The method of claim 17 wherein said step of assaying includes the step of comparing the ratio of the number of living tumor cells to the number of internal standard cells in the portion of the sample exposed to the effector substance with the ratio in a portion of the sample not exposed to the immune effector substance.

19. A method to predict clinical relapse in a patient receiving therapy using an immune effector substance which comprises:
(a) withdrawing a sample containing fresh tumor cells and non-tumor cells including endogenous effector cells from a subject receiving therapy and suspected of undergoing clinical relapse of cancer; and
(b) determining in vitro the response of said tumor cells to the presence of an immune effector substance used in therapy of the subject by determining the number of tumor and normal cells surviving after incubation of a portion of the sample in the presence of the effector substance as compared to the numbers of tumor cells surviving in the absence of the effector substance, by identifying and enumerating the cells that exclude a dye excluded by living cells and normalizing to an internal standard, and counterstaining said cells with a stain that indicates living cells, whereby if said tumor cells are determined in step (b) to have diminished response to the presence of said immune effector substance, clinical relapse of cancer is predicted in said subject.

20. The method of claim 19 wherein said step of determining includes the step of comparing the ratio of the number of living tumor cells to the number of internal standard cells in the portion of the sample exposed to the effector substance with the ratio in a portion of the sample not exposed to the immune effector substance.

* * * * *